(12) United States Patent
Potempa et al.

(10) Patent No.: US 9,150,337 B1
(45) Date of Patent: Oct. 6, 2015

(54) APPLICATOR

(76) Inventors: Michael M. Potempa, Freeport, IL (US); Brian S. Potempa, Freeport, IL (US); Mark Beres, Oconomowoc, WI (US)

( * ) Notice: Subject to any disclaimer, the term of this patent is extended or adjusted under 35 U.S.C. 154(b) by 641 days.

(21) Appl. No.: 13/402,868

(22) Filed: Feb. 22, 2012

Related U.S. Application Data

(60) Provisional application No. 61/446,037, filed on Feb. 23, 2011.

(51) Int. Cl.
A45D 44/16 (2006.01)
B65D 47/42 (2006.01)
A61F 13/40 (2006.01)

(52) U.S. Cl.
CPC .............. *B65D 47/42* (2013.01); *A61M 35/006* (2013.01)

(58) Field of Classification Search
USPC .............. 401/6, 132–135; 15/104.93, 104.94; 222/541.6, 541.9; 206/484
See application file for complete search history.

(56) References Cited

U.S. PATENT DOCUMENTS

| 4,964,744 | A | * | 10/1990 | Whitear ............................ 401/6 |
| 5,013,171 | A | * | 5/1991 | Almond, II ...................... 401/6 |
| 5,341,538 | A | | 8/1994 | Banome |
| 5,573,342 | A | | 11/1996 | Patalano |
| 5,745,949 | A | | 5/1998 | Pine |
| 5,851,077 | A | | 12/1998 | Trejo |
| 5,979,006 | A | | 11/1999 | Stokes et al. |
| 6,250,829 | B1 | | 6/2001 | Brower et al. |
| 6,588,961 | B2 | | 7/2003 | Lafosse-Marin et al. |
| 6,899,481 | B2 | * | 5/2005 | Katsandres et al. .............. 401/6 |
| 7,552,823 | B2 | * | 6/2009 | Schuehrer ..................... 206/484 |

* cited by examiner

Primary Examiner — David Walczak

(57) ABSTRACT

An applicator for applying a substance to a body has a first portion and a second portion. A perforation line extends circumferentially around the applicator and separates the first portion and the second portion. A web is contained within the applicator. The web is attached to the first portion and the second portion, such that when the applicator is ruptured, the web may be used to apply the substance to the body by grasping the first portion and the second portion and manipulating the web on the body.

5 Claims, 3 Drawing Sheets

APPLICATOR

BACKGROUND OF THE INVENTION

The application of a lotion, such as a sun screen lotion or a medicament lotion, may be difficult when applying the lotion to the body. Unless assistance by someone else is obtained, parts of the body may not be adequately covered with the lotion due to the inability of the person to reach areas of his or her own body with the lotion. For example, it is well known that it is extremely difficult to apply a lotion to the back. This problem is further compounded if the person has a physical disability.

Failure to apply a lotion uniformly can result in discomfort, lack of uniformity in color of the skin, and, if the lotion is a medicine, perhaps serious injury. Additionally, a person attempting to apply the lotion to his or her back may waste significant lotion. Some lotions, especially medicament lotions, are expensive.

Prior inventions have attempted to address the problem.

For example, in U.S. Pat. No. 7,597,494 (Migyanka), utilizes a cable placed inside the lotion container. Part of the cable is accessible outside of the container, allowing a user to pull the cable from the container. The cable carries the lotion outside of the container. The user then applies the lotion by stretching the cable across his or her back and moving the cable up and down.

In U.S. Pat. No. 6,250,829 (Bower et al.), a storage and applicator uses a thin, fabric like cavity applicator that is pre-impregnated with fluid. Upon opening the enclosure, a user inserts his or her hand in the applicator and spreads the fluid over his or her body.

The problem with these inventions is that they are inconvenient to use and expensive to manufacture.

BRIEF SUMMARY OF THE INVENTION

The present invention is a device for the self application of lotion or a fluid medicament to the surface of the human body.

A towel is contained within a container portion of a package. The package could be, for example, a plastic squeeze container. The container portion is filled with a cream, ointment, or lotion such as a medicament or sun tan lotion. The towel is impregnated with the cream, ointment or lotion contained within the container portion. The package could be plastic or other suitable material.

The package preferably includes handles at either of its distal ends. The container portion includes a perforation extending axially about the container portion. The towel is affixed to both ends of the package. A portion of the towel is contained within the container portion of the package.

In order to access the towel, the container portion is torn on the perforation such as to detach one end of the container portion for the other. The handles of the package are grasped. The towel contained within the container portion is unfolded and extended.

A person holder the ends of the package can stretch the towel to a suitable length. A person then positions the towel at a particular location and moves the towel up and down or left to right in a manner to properly deposition the contents of the container portion onto the skin.

Thus, difficult to reach spots such as the back and behind the legs can be easily covered with the lotion or ointment. After the desired application of the lotion or ointment is complete, the entire package can be suitable disposed of.

The towel could be an elastic or non-elastic material such as a polyester filament which is adsorbent and readily adheres to lotions.

An object of the present invention is to provide a means for the easy self application of a lotion or medicament to those more inaccessible parts of the human body such as the back, especially for those individuals with restricted range of motion such as the disabled or elderly.

Another object of the present invention is to provide a means for applying a carefully measured amount to lotion or medicament to the surface of the human body without waste.

A further object of the present invention is to provide a means for evenly distributing lotion or medicament over the human body.

The applicant is not aware of any previously described art having the features and advantages of the present invention.

Other objects and advantages of the present invention will become apparent from the following descriptions, taken in connection with the accompanying drawings, wherein by way of illustration and example, a preferred embodiment of the present invention is disclosed.

DETAILED DESCRIPTION OF THE INVENTION

Figure 1:
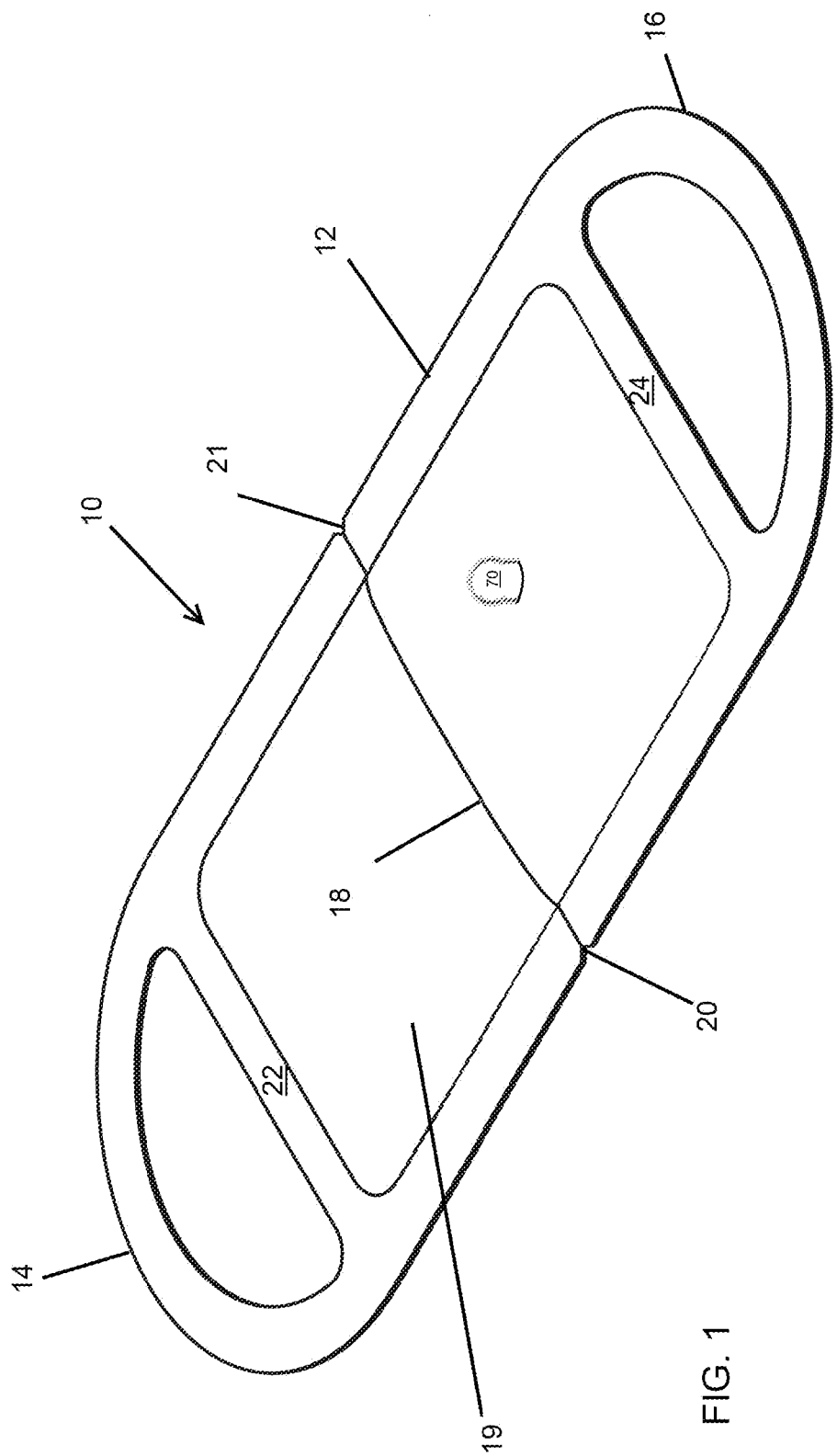
FIG. 1 is a perspective view of the present invention where the container has not been opened.

FIG. 1 is a perspective view of the present invention 10 where the packaging has not been opened. The invention includes a package 12 filled with a cream, ointment, gel or lotion such as a medicament or sun tan lotion. The package 12 could be plastic or other suitable material.

At the end of the package 12 are the handles 14, 16. The handles 14, 16 are shown to be semi-circular in design. However, the handles 14, 16 could be of any design suitable for grasping, such as a straight, linear handle or a handle with some type of resistive device to assist in holding the handle. The handles 14, 16 can also be used to hang the packages in a display. A first bridge 22 and a second bridge 24 extend across the package 12.

A perforation 18 is positioned between the handles 14, 16 within the container portion 19 of the package 12. The perforation 18 extends across the container portion 19. The package 12 also includes a first indentation 20 on one side of the package 12 and a second indentation 21 on the other side of package 12. The container portion 19 contains a reservoir. The reservoir contains a substance such a cream, ointment, or lotion to be spread upon the outer surface of the body.

In order to release the cream, ointment or lotion within the container portion 19 of the package 12, a person grasps the package 12 and tears the perforation at either of the two indentations. When it is completely torn, the package 12 may then be opened by grasping the handles 14, 16 and pulling the package 12 into two pieces.

Figure 2:
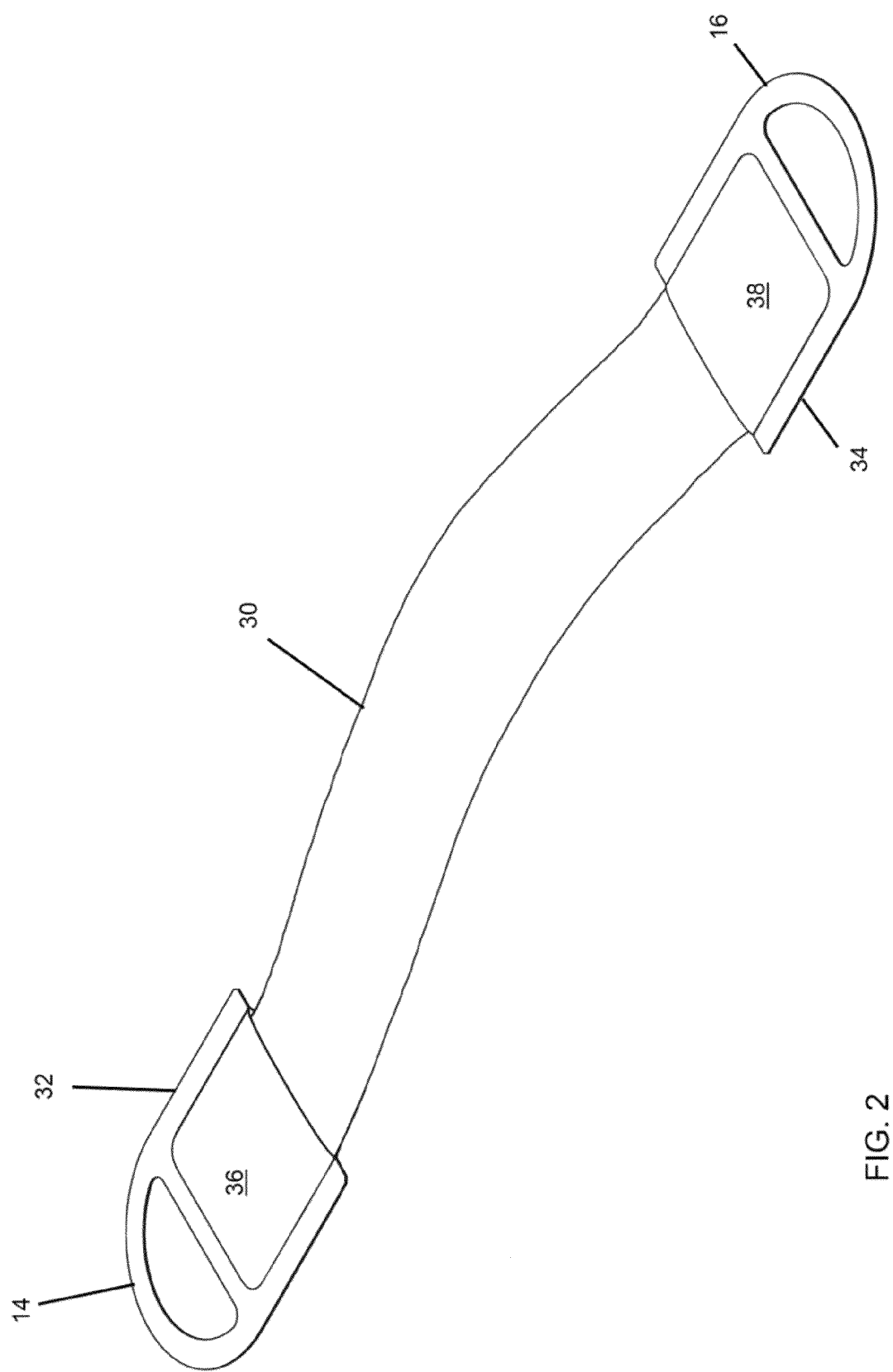
FIG. 2 is a perspective view of the present invention where the container has been opened.

FIG. 2 shows the present invention after the package 12 has been opened. Within the package 12 is a web 30. The web 30 could be made of cloth, gauze, foam or any other material which is adapted to retain and spread lotion. The web 30 is impregnated with the cream, ointment, or lotion that was within the container portion.

The package 12 has been split into a first package part 32 and a second package part 34. The container portion 19 has been split into a first container portion 36 and a second container portion 38.

The web 30 is of sufficient length to allow a person to grasp the handle 14 with one hand and the handle 16 by the other hand. Then, a person can position the web 30 behind the back, leg or some other difficult to reach area of the body, and may move the towel up and down and across the back of the person. Obviously, the web 30 could have different lengths and widths depending upon the particular desired use of the invention.

Figure 3:
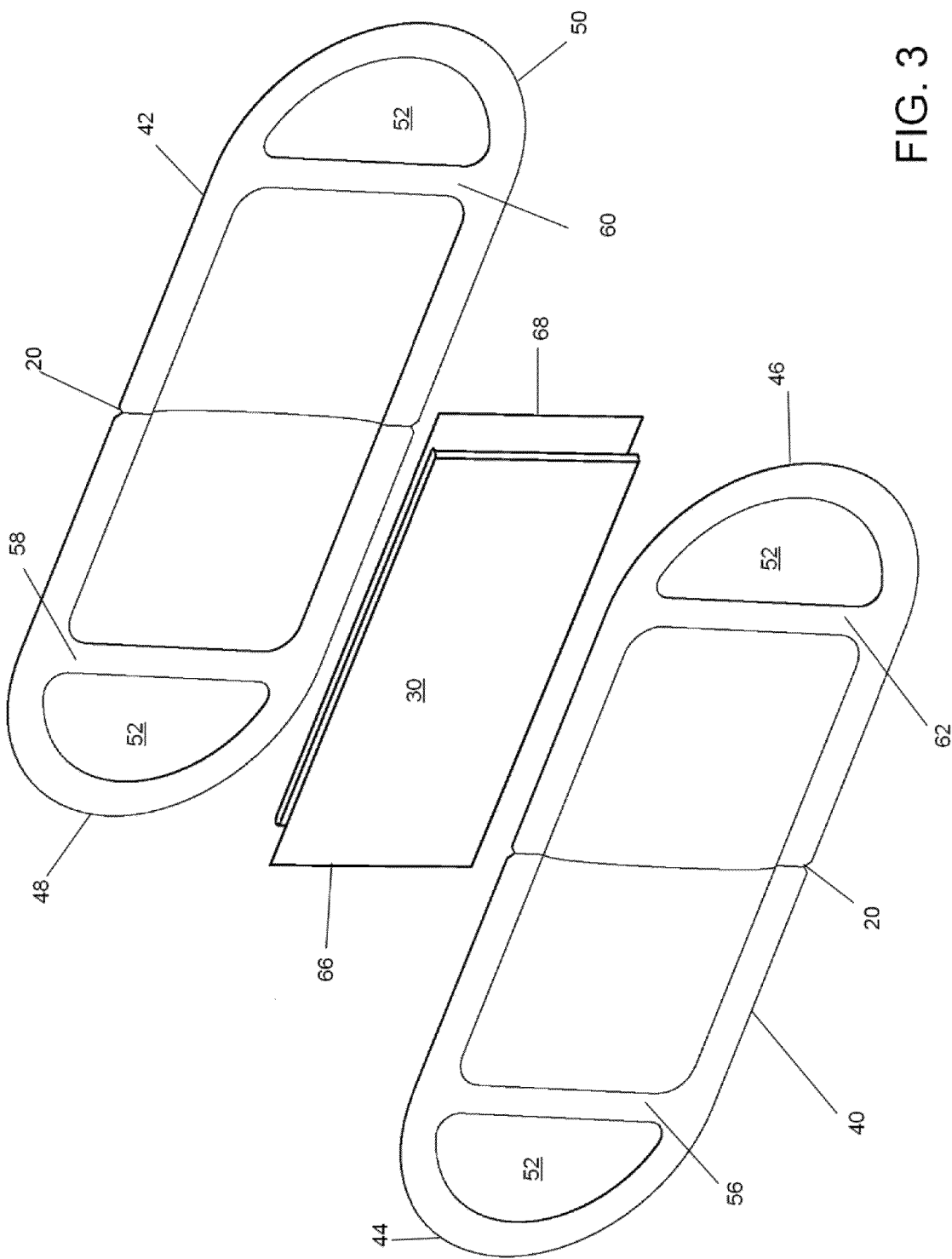
FIG. 3 is a perspective view of the present invention where the container has not been opened.

FIG. 3 is an exploded view of the present invention. The package 12 is formed of an upper portion and a lower portion. The handles 14, 16 have upper handle portions 44, 46 and lower handles portion 48, 50. The areas marked 52 are voids, thereby giving the handles 14, 16 a generally semi-circular appearance. A person can extend a portion of his or her fingers through the voids 52 in order to securely grasp the handles 14, 16.

The first bridge 22 has a first bridge upper portion 56 and a first bridge lower portion 58. The second bridge 24 has a second bridge upper portion 62 and a second bridge lower portion 60. The web 30 has a first distal end 66 and a second distal end 68.

In order to manufacture the package 12, the web 30 is placed within the container portion 19. The first distal end 66 of the web 30 is position so as to be between the first bridge upper portion 56 and the first bridge lower portion 58. Similarly, the second distal end 68 of the web 30 is positioned between the second bridge upper portion 62 and the second bridge lower portion 60.

The package 12 is sealed. The first bridge upper portion 56 is heat sealed to the first bridge lower portion 58, thereby securing the first distal end 66 of the web 30. Similarly, the second bridge upper portion 62 and the second bridge lower portion 60 are heat sealed, thereby securing the second distal end 68 of the web 30.

The lotion, cream, gel, or ointment could be injected into the container portion 19 prior to sealing on four sides of the package 12. Alternatively, the lotion, cream, gel or ointment could be saturated into the towel prior to sealing.

The voids 52 are removed by stamping after the package is sealed.

The invention could be used with any topical preparation such as creams, gels, ointments, or lotions.

While the invention has been described in connection with only two embodiments of alternate sealing configurations, it is not intended to limit the scope of the invention to the particular form set forth, but on the contrary, it is intended to cover such alternatives, modifications, and equivalents.

Referring again to FIG. 1, the applicator may have a removable nipple 70. The nipple 70 is positioned such that the nipple can be removed, allowing the substance to be released from the container portion 19. The nipple 70 could be placed on the perforation line 18.

We claim:

1. An applicator for applying a substance to a body surface of a user comprising:
   a container portion for receivably containing the substance therein, and a web contained within the container portion, the web physically attached to the applicator, the applicator having a first end and a second end, the second end being distal from the first end, the web physically attached to the first end and the second end, the applicator having a perforation line extending circumferentially about the applicator, such that when the applicator line is ruptured, the applicator may be be split into a first part and a second part, the first part being attached to the second part by the web.

2. The applicator of claim 1 where the applicator includes a first handle and a second handle, the first handle located proximal to the first end and the second handle located proximal to the second end.

3. The applicator of claim 2 where the web has an extended length which is greater than the length of the container portion.

4. An applicator for applying a substance to a body surface of a user comprising:
   an upper portion and a lower portion, the upper portion and lower portion each having a perimeter, the upper and lower portions sealed to form a container portion within the upper portion and the lower portion, the container portion for containing the substance and the container portion having a first end and a second end, the first end of the container portion being distal from the second end of the container portion; and a web positioned between the upper portion and lower portion such that when the container portion is filled with a substance, the substance is in contact with a substantial portion of the web, the web having a first web end and a second web end, the first web end connected between the upper portion and the lower portion at the first end of the container portion, and the second web end also connected between the upper portion and the lower portion at the second end of the container portion, the applicator having a perforation line extending circumferentially about the container portion, such that when the applicator line is torn, the applicator may be split into a first part and a second part, the first part being attached to the second part by the web.

5. The applicator of claim 4 where a first handle is attached to the upper portion and the lower portion near the first end of the container portion, and a second handle is attached to the upper portion and the lower portion near the second end of the container portion.

* * * * *